(12) United States Patent
Vidal et al.

(10) Patent No.: US 6,379,395 B1
(45) Date of Patent: Apr. 30, 2002

(54) PYRAZOLOPYRIMIDINOXO-CONTAINING COMPOSITIONS FOR DYEING KERATIN FIBRES; THEIR USE IN DYEING AS COUPLERS; DYEING PROCESSES

(75) Inventors: Laurent Vidal, Paris; Gérard Malle, Villiers sur Morin, both of (FR)

(73) Assignee: L'Oreal S.A. (FR)

(*) Notice: Subject to any disclaimer, the term of this patent is extended or adjusted under 35 U.S.C. 154(b) by 0 days.

(21) Appl. No.: 09/668,742

(22) Filed: Sep. 25, 2000

Related U.S. Application Data

(63) Continuation of application No. 09/155,211, filed as application No. PCT/FR97/00506 on Mar. 21, 1997, now Pat. No. 6,179,882.

(30) Foreign Application Priority Data

Mar. 22, 1996 (FR) .............................................. 96/03629

(51) Int. Cl.$^7$ ................................................ A61K 7/13
(52) U.S. Cl. ....................... 8/405; 8/409; 8/423; 8/567; 8/573
(58) Field of Search ............................ 8/409, 423, 567, 8/573, 405, 467

(56) References Cited

U.S. PATENT DOCUMENTS

| | | | |
|---|---|---|---|
| 3,061,432 A | 10/1962 | Menzel et al. | 430/376 |
| 3,227,554 A | 1/1966 | Barr et al. | 430/382 |
| 3,419,391 A | 12/1968 | Young | 430/387 |
| 3,725,067 A | 4/1973 | Bailey et al. | 430/476 |
| 3,820,948 A | 6/1974 | Berth | 8/409 |

(List continued on next page.)

FOREIGN PATENT DOCUMENTS

| | | |
|---|---|---|
| DE | 2 160 317 | 6/1973 |
| DE | 2 359 999 | 6/1975 |
| DE | 3 731 395 | 4/1989 |
| DE | 3 843 892 | 6/1990 |
| DE | 4 009 097 | 9/1991 |

(List continued on next page.)

OTHER PUBLICATIONS

R. Stollé, "Ueber die Ueberführung der secundären Säurehydrazide in Derivate des Furodiazols, Pyrrodiazols und Thiodiazols", Chemischen Gesellschaft, pp. 797–798, 1899.
Hans Beyer et al., "Über die Pyrazolbildung aus α–Chlor–acetessigester und Thiocarbohydazid", Chemische Berichte, pp. 2550–2555, 1956.
H. Wilde et al., Synthese von 4H–Pyrazolo[1,5–a]benzimidazolen, Journal Für Praktische Chemie, pp. 829–836, 1984.
Lidia Wyzgowska et al., "O Reakcjach Trikarboetoksymetanu VIII", Acta Poloniae Pharmaceutica, pp. 83–88, 1982.
E. Hannig et al., "Zur Kenntnis des 4–aminierten Phenylbutazons", Die Pharmazie, pp. 231, 1980.

Giuliana Cardillo et al., "Su due constituenti minori della Kamala", Gazetta Chimica Italiana, pp. 725–734, 1965.
Thomas Kauffmann et al., Synthese von Amidrazonon aus Nitrilen und Natriumhydrazid, pp. 3436–3443, 1964.
von Helmut Dorn et al., "Synthese und Methylierung von 1H–Pyrazolo[3,4–b]pyrazinen, einer neuen Klasse von Purin–Antagonisten", Annalen der Chemie, pp. 118–123, 1968.
von Helmut Dorn et al., "Über die elektrophile Substitution von 3(5)–Amino–pyrazol", Annalen der Chemie, pp. 141–146, 1967.
Mohamed Helmi Elnagdi et al., "Studies on 3,5–pyrazolidinediones. IV. Addition of 4–Arylazo–3,5–pyrazolidinediones to Ethyl Acrylate", Bulletin of Them Chemical Society of Japan, vol. 46, pp. 1830–1833, 1973.
Günther Ege et al., "A Simple Synthesis of 3(5)–Aminopyrazole", Angew. Chem. internat. Edit, vol. 13, No. 3, pp. 206–207, 1974.
Kazumasa Takahashi et al., "Syntheses of 3(5)–Substituted–4–(N–methylanilino)–5(3)–aminopyrazoles by Reaction of β–Hydroxy–α–cyano–enamines with Hydrazines", Journal of Synthetic Organic Chemistry, No. 8, pp. 794–796, 1985.
Chiara B. Vincentini et al., "Pyrazolo[3,4–d][1,2,3]Triazole–1–carboxamides and 5–Alkylaminopyrazolo[3,4–d]oxazoles: Synthesis and Evaluation of the in Vitro Antifungal Activity", II Farmaco, Vo. 47, No. 7, 8, pp. 1021–1034, 1992.

(List continued on next page.)

Primary Examiner—Lorna M. Douyon
Assistant Examiner—Eisa Elhilo
(74) Attorney, Agent, or Firm—Finnegan, Henderson, Farabow, Garrett & Dunner, L.L.P.

(57) ABSTRACT

The present invention relates to a composition for dyeing keratin fibers, in particular human hair, containing, in a medium which is suitable for dyeing:

as coupler, at least one compound of formula:

(I)

or one of the addition salts with an acid, with
   $R_1$ denotes, in particular, hydrogen, alkyl, aryl, a heterocycle, halogen,
   $R_2$ denotes, in particular, hydrogen, halogen, alkoxy, aryloxy, acyloxy, arylthio, alkylthio, . . .
   $R_3$ has the same meanings as those for $R_1$,
   $Z_a$ and $Z_b$, which are different, denote C=O or $CR_4$, with $R_4$ having the same meanings as $R_1$;
and at least one oxidation base.

31 Claims, No Drawings

U.S. PATENT DOCUMENTS

| | | | | |
|---|---|---|---|---|
| 3,926,631 | A | 12/1975 | Arai et al. | 430/226 |
| 4,128,425 | A | 12/1978 | Greenwald | 430/440 |
| 4,293,543 | A | 10/1981 | Cotte et al. | 8/405 |
| 4,500,630 | A | 2/1985 | Sato et al. | 430/386 |
| 5,256,526 | A | 10/1993 | Suzuki et al. | 430/384 |
| 5,441,863 | A | 8/1995 | Tang et al. | 430/558 |
| 5,457,210 | A | 10/1995 | Kim et al. | 548/262 |
| 5,785,720 | A | 7/1998 | Eichenberger et al. | 8/567 |
| 6,099,593 | A * | 8/2000 | Terranova et al. | 8/409 |

FOREIGN PATENT DOCUMENTS

| | | |
|---|---|---|
| DE | 4 133 957 | 4/1993 |
| EP | 0 030 680 | 6/1981 |
| EP | 0 119 860 | 9/1984 |
| EP | 0 285 274 | 10/1988 |
| EP | 0 304 001 | 2/1989 |
| EP | 0 309 652 | 4/1989 |
| EP | 0 320 764 | 6/1989 |
| EP | 0 456 226 | 11/1991 |
| EP | 00488 248 | 6/1992 |
| EP | 0 488 909 | 6/1992 |
| EP | 0 518 238 | 12/1992 |
| EP | 0 547 864 | 6/1993 |
| EP | 0 557 851 | 9/1993 |
| EP | 0 578 248 | 1/1994 |
| EP | 0 591 103 | 4/1994 |
| FR | 1 564 999 | 4/1969 |
| FR | 2 075 583 | 10/1971 |
| FR | 2 466 492 | 4/1981 |
| FR | 2 486 913 | 3/1987 |
| GB | 1 026 978 | 3/1963 |
| GB | 1 153 196 | 6/1966 |
| GB | 1 458 377 | 9/1974 |
| JP | 58 42045 | 3/1983 |
| JP | 59 99437 | 6/1984 |
| JP | 59 162548 | 9/1984 |
| JP | 59 171956 | 9/1984 |
| JP | 60 33552 | 2/1985 |
| JP | 60 43659 | 3/1985 |
| JP | 60 172982 | 9/1985 |
| JP | 60 190779 | 9/1985 |
| JP | 62 79337 | 12/1987 |
| JP | 63 169571 | 7/1988 |
| JP | 62 36011 | 8/1994 |
| JP | 70 36159 | 2/1995 |
| JP | 70 84348 | 3/1995 |
| JP | 7 92632 | 4/1995 |
| WO | WO 92/04349 | 3/1992 |
| WO | WO 92/04883 | 4/1992 |
| WO | WO 94/04130 | 3/1994 |
| WO | WO 94/08959 | 4/1994 |
| WO | WO 94/08969 | 4/1994 |
| WO | WO 94-89970 | 4/1994 |

OTHER PUBLICATIONS

Edward C. Taylor et al., "The Reaction of Malononitrile with Substituted Hydrazines: New Routes to 4–Aminopyrazolo[3,4–d]pyrimidines", Journal of the merican Chemical Society, vol. 81, No. 10, pp. 2456–2464, 1959.

C.B. Vincentini et al., "A New Fused Heterocyclic System: 6H–Pyrazolo[3,4–c][1,2,5]thiadizine 2,2–Dioxide", Journal of Heterocyclic Chemistry, vol. 26, No. 3, pp. 797–803, 1989.

E.J. Browne et al., "Triazoles. Part VII. Syntheses of Substituted 1,2,4–Triazoles", Journal of The Chemical Society, pp. 5149–5152, 1962.

Philip Magnus et al., "Synthesis of helical Poly–β–pyrroles. Multiple Atropisomerism Resulting in Helical Enantiomorphic Conformations", Journal of the American Chemical Society, vol. 112, No. 6, pp. 2465–2468, 1990.

Paul Carter et al., "Studies on the Synthesis of the Antitumor Agent CC–1065. Synthesis of PDE I and PDE II, Inhibitors of Cyclic Adenosine–3',5'–monophosphate Phosphodiesterase Using the 3,3'–Bipyrrole Strategy", Journal of the American Chemical Society, vol. 109, No. 9, pp. 2711–2717, 1987.

H. Koopman, "Investigations on Herbicides IV, The synthesis of 2,6–dichlorobenzonitrile", Recueil, vol. 80, No. 9–10, pp. 1075–1083, 1961.

Joseph Bailey, "Synthesis of 1H–Pyrazolo[3,2-c]–s–Triazoles and Derived Azamethine Dyes", Journal of the Chemical Society, pp. 2047–2052, 1977.

Mohamed Helmy Elnagdi et al., "Routes for the Synthesis of 3,5–Diaminopyrazoles, 2–Aminopyrazolo[1,5–a]pyrimidines and 5–Aminopyrazolo[1,5–a]pyramidines", Jounral f. prakt. chemie, Band 320, heft 4, pp. 533–538, 1978.

* cited by examiner

PYRAZOLOPYRIMIDINOXO-CONTAINING COMPOSITIONS FOR DYEING KERATIN FIBRES; THEIR USE IN DYEING AS COUPLERS; DYEING PROCESSES

This is a continuation of application Ser. No. 09/155,211, filed Jun. 16, 1999, U.S. Pat. No. 6,179,882 as a national stage application under 35 U.S.C. § 371 of International Application No. PCT/FR97/00506, filed Mar. 21, 1997.

The invention relates to a composition for the oxidation dyeing of keratin fibres, in particular human hair, containing at least one pyrazolopyrimidinoxo compound as coupler and at least one oxidation base.

It is known to dye keratin fibres, and in particular human hair, with dye compositions containing oxidation dye precursors, in particular ortho- or para-phenylene diamines, ortho- or para-aminophenols, and heterocyclic compounds, which are generally referred to as oxidation bases. Oxidation dye precursors, or oxidation bases, are colourless or weakly coloured compounds which, when combines with oxidizing products, can give rise to coloured compounds and dyes by a process of oxidative condensation.

It is also known that the shades obtained with these oxidation bases can be varied by combining them with couplers or colour modifiers, the latter being chosen in particular from aromatic meta-diamines, meta-aminophenols, meta-diphenols and certain heterocyclic compounds such as indole compounds.

The variety of molecules used as oxidation bases and couplers allows a wide range of colours to be obtained.

The so-called "permanent" coloration obtained by means of these oxidation dyes must moreover satisfy a certain number of requirements. Thus, it must have no toxicological drawbacks, it must be able to allow shades to be obtained in the desired intensity and it must show good resistance to external agents (light, bad weather, washing, waving, permanent-waving, perspiration, rubbing).

The dyes must also be able to cover grey hair and, lastly, they must be as unselective as possible, i.e. they must allow only the smallest possible colour differences to be obtained along the length of the same keratin fibre, which may, indeed, be differently sensitized (i.e. damaged) between its tip and its root.

The Applicant has now discovered that it is possible to obtain novel, powerful, unselective and particularly resistant dyes, which are capable of giving rise to intense colorations in varied shades, by using pyrazolopyrimidinoxo compounds as couplers in the presence of an oxidation base.

This discovery forms the basis of the present invention.

The subject of the invention is a composition for dyeing keratin fibres, and in particular human keratin fibres such as the hair, characterized in that it comprises, in a medium which is suitable for dyeing:

as coupler, at least one pyrazolopyrimidinoxo compound of formula (I), or one of the addition salts thereof with an acid:

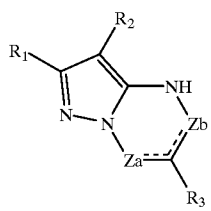

(I)

in which:

$R_1$ represents: a hydrogen atom, a linear or branched $C_1$–$C_{20}$ alkyl radical optionally substituted with 1 or 2 radicals R chosen from the group consisting of halogen, nitro, cyano, hydroxyl, alkoxy, aryloxy, amino, alkylamino, acylamino, carbamoyl, sulphonamido, sulphamoyl, imido, alkylthio, arylthio, aryl, alkoxycarbonyl, aryl; an aryl radical (such as phenyl or naphthyl) optionally substituted with 1 or 2 radicals R as defined above; a 5- or 6-membered heterocycle having at least one nitrogen, oxygen or sulphur atom (such as pyridyl, quinolyl, pyrrolyl, morpholyl, furyl, tetrahydrofuryl, pyrazolyl, triazolyl, tetrazolyl, thiazolyl, oxazolyl, imidazolyl or thiadiazolyl) optionally substituted with 1 or 2 radicals R as defined above;

when $R_1$ denotes an alkyl radical, an aryl radical or a 5- or 6-membered heterocycle (defined above), it can be linked to the carbon atom of the ring via an oxygen, nitrogen or sulphur atom (in this case, $R_1$ becomes $XR_4$ with X=O, NH, S);

$R_1$ can also denote a halogen atom (such as bromine, chlorine or fluorine); an acyl radical, a sulphonyl radical; a sulphinyl radical; a phosphonyl radical, a carbamoyl radical, a sulphamoyl radical, a cyano radical, a siloxy radical, an amino radical; an acylamino radical; an acyloxy radical; a carbamoyloxy radical, a sulphonamide radical; an imide radical, a ureido radical; a sulphamoylamino radical; an alkoxycarbonylamino radical; an aryloxycarbonylamino radical; an alkoxycarbonyl radical; an aryloxycarbonyl radical, a carboxyl radical;

$R_2$ represents; a hydrogen atom; a halogen atom such as bromine, chlorine or fluorine, an aretylamido group; an alkoxy radical (such as, for example methoxy, ethoxy, propyloxy, benzyloxy, methoxyethoxy, phenoxyethoxy, 2-cyanoethoxy, phenethyloxy, p-chlorobenzyloxy, methoxyethylcarbamoylmethoxy); an aryloxy radical (such as, for example: phenoxy, 4-methoxyphenyl, 4-nitrophenoxy, 4-cyanophenoxy, 4-methanesulphonamidophenoxy, 4-methanesulphonylphenoxy, 3-methylphenoxy, 1-naphthyloxy); an acyloxy radical (such as, for example, acetoxy, propanoyloxy, benzoloxy, 2,4-dichlorobenzoyloxy, ethoxyalkyloxy, pyruvyloxy, cinnamoyloxy, myristyloxy); an arylthio radical (such as, for example: phenylthio, 4-carboxyphenylthio, 4-methanesulphonylphenylthio); an alkylthio radical (such as, for example: methylthio, ethylthio, propylthio, butylthio, 2-cyanoethylthio, benzylthio, phenethylthio, 2-(diethylamino)ethylthio, ethoxyethylthio, phenoxyethylthio); a heteroarylthio radical (such as, for example, 5-phenyl-2,3,4,5-tetrazolylthio, 2-benzothiazolylthio); a heteroaryloxy radical (such as, for example: 5-phenyl-2,3,4,5-tetrazolyloxy, 2-benzothiazolyloxy); a thiocyano radical; an N,N-diethylthiocarbonylthio radical; a dodecyloxythiocarbonylthio radical; a benzenesulphonamido radical; an N-ethyltoluenesulphonamido radical; a pentafluorobutanamido radical, a 2,3,4,5,6-pentafluorobenzamido radical; a p-cyanophenylureido radical; an N,N-diethylsulphamoylamino radical; a pyrazolyl radical; an imidazolyl radical; a triazolyl radical, a tetrazolyl radical; a benzimidazolyl radical; a 1-benzyl-5-ethoxy-3-hydrantoinyl radical, a 1-benzyl-3-hydrantoinyl radical; 5,5-dimethyl-2,4-dioxo-3-oxazolidinyl; a 2-oxy-1,2-dihydro-1-pyridyl radical; an alkylamido; an arylamido; a radical $NR'''R^{IV}$ with $R'''$ and $R^{IV}$, which may be identical or different, representing a $C_1$–$C_4$ alkyl, a hydroxyalkyl, a carboxyl; or an alkoxycarboxylic radical;

$R_1$ has the same meanings mentioned as those mentioned for the radical $R_1$;

$Z_a$ and $Z_b$ are different and represent a C=O group or a carbon atom bearing a radical $R_4$ having the same meanings as those mentioned for the radical $R_1$;

and at least one oxidation base.

The addition salts with an acid for the compounds of the invention can be chosen in particular from hydrochlorides, hydrobromides, tartrates, tosylates, benzenesulphonates, sulphates, lactates and acetates.

Among the radicals $R_1$ of formula (I) defined above, the preferred radicals are chosen from the group consisting of:

a hydrogen atom; a linear or branched $C_1$–$C_4$ alkyl; a phenyl, a phenyl substituted with a halogen atom; a $C_1$–$C_4$ alkyl, a $C_1$–$C_4$ alkoxy, a nitro group, an amino group, a trifluoromethyl group or a $C_1$–$C_4$ alkylamino group, a benzyl, radical, a benzyl radical substituted with a halogen atom, a $C_1$–$C_4$ alkyl, a $C_1$–$C_4$ alkoxy, a nitro group, an amino group, a trifluoromethyl group, a $C_1$–$C_4$ alkylamino, a heterocycle chosen from thiophene, furan and pyridine, a trifluoromethyl radical; a radical $(CH_2)_p$—X—$(CH_2)_q$—OR' where p and q are integers, which may be identical or different, between 1 and 3, R' represents H or methyl and X denotes an oxygen atom or a group NR' with R" denoting hydrogen or methyl; a $C_1$–$C_4$ hydroxyalkyl; a $C_1$–$C_4$ aminoalkyl; a $C_1$–$C_4$ alkylamino; a $C_1$–$C_4$ dialkylamino; a phenyloxycarbonyl; methylthio, ethylthio; phenylthio; methanesulphonyl; cyano; an arylamino; an alkoxy radical chosen from methoxy, ethoxy, phenoxy, a halogen chosen from chlorine, bromine, fluorine, a carboxyl group; a ($C_1$–$C_4$) alkoxycarbonyl.

Among the radicals $R_1$ of formula (I) defined above, the radicals more particularly preferred are chosen from the group consisting of:

hydrogen; an alkyl chosen from methyl, ethyl, isopropyl, tert-butyl; a halogen chosen from fluorine and chlorine, phenyl, tolyl; 4-chlorophenyl; 4-methoxyphenyl; 3-methoxyphenyl; 2-methoxyphenyl; benzyl; a heterocycle chosen from pyridyl, furyl and thienyl, trifuoromethyl, hydroxymethyl; aminomethyl, methoxy or ethoxy; methylamino or ethylamino or dimethylamino; carboxyl; methoxycarbonyl or ethoxycarbonyl; cyano.

Even more particularly, the preferred radicals $R_1$ are chosen from the group consisting of hydrogen, methyl, ethyl, phenyl, tolyl, 4-chlorophenyl; 4-methoxyphenyl; benzyl; trifluoromethyl; chloro; a methoxy or ethoxy radical; a carboxyl radical; methylamino or dimethylamino; cyano.

Among the radicals $R_2$ of formula (I) defined above, the preferred radicals are chosen from the group consisting of:

a hydrogen atom, a $C_1$–$C_4$ alkoxy; phenoxy; phenoxy substituted with a halogen atom, a $C_1$–$C_4$ alkyl, a carboxyl, a trifluoromethyl group; an acyloxy radical; benzyloxy; $C_1$–$C_4$ alkylthio, phenylthio; phenylthio substituted with a halogen atom, a $C_1$–$C_4$ alkyl, a carboxyl, a trifluoromethyl group; a $C_1$–$C_4$ alkylamino; phenylamido, a radical $NR^{III}R^{IV}$ with $R^{III}$ and $R^{IV}$, which may be identical or different, representing a $C_1$–$C_4$ alkyl, a $C_1$–$C_4$ hydroxyalkyl; a carboxyl; a $C_1$–$C_4$ alkoxycarboxylic radical.

Among the radicals $R_1$ of formula (I) defined above, the radicals more particularly preferred are chosen from the group consisting of:

hydrogen; chlorine or bromine; methoxy or ethoxy; phenoxy; 4-methylphenoxy; acyloxy; benzyloxy; methylthio or ethylthio; phenylthio; 4-methylphenylthio; 2-tert-butylphenylthio; acetamido; phenylacetamido; dimethylamino; diethylamino; ethylemthylamino; (β-hydroxyethyl)methylamino.

Even more particularly, the preferred radicals $R_2$ are chosen from the group consisting of:

hydrogen; chlorine; ethoxy; phenoxy; benzyloxy; acyloxy; acetamido; dimethylamino.

Among the radicals $R_3$ and $R_4$ of formula (I) defined above, the preferred radicals are chosen from the group consisting of:

a hydrogen atom; a linear or branched $C_1$–$C_4$ alkyl optionally substituted with a hydroxy or amino; a phenyl; a phenyl substituted with one or two groups chosen from a halogen, a $C_1$–$C_4$ alkyl, a $C_1$–$C_4$ alkoxy; a hydroxyl; a carboxyl, a nitro group, a $C_1$–$C_4$ alkylthio, a methylenedioxy group, an amino group, a trifluoromethyl group or a $C_1$–$C_4$ alkoxylamino, a benzyl radical; a benzyl radical substituted with a halogen atom, a methyl or isopropyl, methoxy; a $C_1$–$C_4$ hydroxyalkyl, a $C_1$–$C_4$ aminoalkyl, a $C_1$–$C_4$ alkylaminoalkyl, an amino radical; a $C_1$–$C_4$ alkylamino radical, a halogen such as chlorine or bromine; a trifluoromethyl.

Among the radicals $R_1$ and $R_4$, the preferred radicals are chosen from the group consisting of:

hydrogen; $C_1$–$C_4$ alkyl (such as methyl, ethyl; isopropyl); halogen (such as chlorine, bromine); amino; $C_1$–$C_4$ alkylamino (such as methylamino, ethylamino or dimethylamino); an aryl radical (such as phenyl, tolyl, 2-, 3- or 4-chlorophenyl, 3- or 4-hydroxyphenyl, 3- or 4-aminophenyl, 3- or 4-methoxyphenyl, 4-trifluoromethylphenyl); benzyl; hydroxymethyl or hydroxyethyl; aminomethyl or aminoethyl, trifluoromethyl.

Even more particularly, the preferred radicals $R_1$ and $R_4$ are chosen from the following radicals:

hydrogen, methyl, ethyl, isopropyl, trifluoromethyl, chlorine, amino, methylamino, ethylamino, phenyl, 4-chlorophenyl, 4-methoxyphenyl.

Among the preferred compounds of the invention of formula (I), mention may be made of those chosen from the group consisting of:

(i) pyrazolo[1,5-a]pyrimidin-7-oxo compounds of formula:

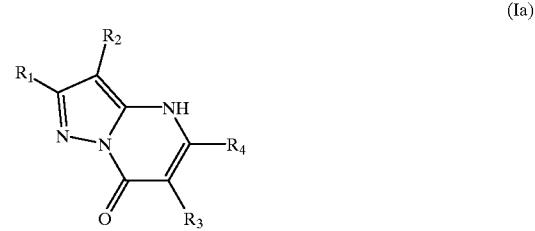

(Ia)

(ii) pyrazolo[1,5-a]pyrimidin-5-oxo compounds of formula:

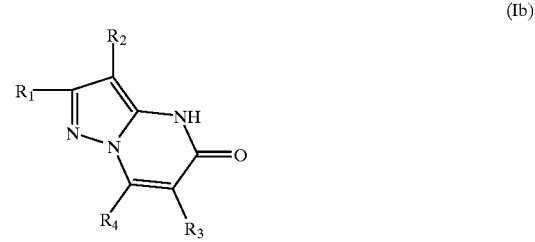

(Ib)

in which the radicals $R_1$, $R_2$, $R_1$ and $R_4$ have the same meanings as those mentioned above.

As examples of compounds of formula (Ia), mention may be made of those for which:

$R_1$ denotes hydrogen, methyl, ethyl, chlorine, phenyl, methoxy, trifluoromethyl, carboxyl or cyano;

$R_2$ denotes hydrogen, chlorine or ethoxy, $R_1$ and $R_4$ respectively denote: hydrogen and hydrogen; hydrogen and methyl; methyl and hydrogen; hydrogen and amino; chlorine and methyl, chlorine and amino; carboxyl and methyl; hydrogen and trifluoromethyl, or carboxyl and hydrogen.

As compounds of formula (Ia) above, mention may be made most particularly of:
pyrazolo[1,5-a]pyrimidin-7-one,
2-methylpyrazolo[1,5-a]pyrimidin-7-one,
2-phenylpyrazolo[1,5-a]pyrimidin-7-one,
2-carboxypyrazolo[1,5-a]pyrimidin-7-one,
2-ethylthiopyrazolo[1,5-a]pyrimidin-7-one,
2,5-dimethylpyrazolo[1,5-a]pyrimidin-7-one,
2-phenyl-5-methylpyrazolo[1,5-a]pyrimidin-7-one,
2-carboxy-5-methylpyrazolo[1,5-a]pyrimidin-7-one,
2-ethylthio-5-methylpyrazolo[1,5-a]pyrimidin-7-one,
2-methyl-5-trifluoromethylpyrazolo[1,5-a]pyrimidin-7-one,
2-phenyl-5-trifluoromethylpyrazolo[1,5-a]pyrimidin-7-one,
2-carboxy-5-trifluoromethylpyrazolo[1,5-a]pyrimidin-7-one,
2-ethylthio-5-trifluoromethylpyrazolo[1,5-a]-pyrimidin-7-one,
5-trifluoromethylpyrazolo[1,5-a]pyrimidin-7-one,
5-methylpyrazolo[1,5-a]pyrimidin-7-one,
6-carboxypyrazolo[1,5-a]pyrimidin-7-one,
6-carboxy-2-methylpyrazolo[1,5-a]pyrimidin-7-one,
6-carboxy-2-phenylpyrazolo[1,5-a]pyrimidin-7-one,
6-carboxy-2-ethylthiopyrazolo[1,5-a]pyrimidin-7-one,
2,6-dicarboxypyrazolo[1,5-a]pyrimidin-7-one,
2-methyl-6-ethoxycarbonylpyrazolo[1,5-a]pyrimidin-7-one,
2-(2'-furyl)-6-methylpyrazolo[1,5-a]pyrimidin-7-one,
2-(2'-thienyl)-6-methylpyrazolo[1,5-a]pyrimidin-7-one,
3-ethyoxycarbonyl-6-methylpyrazolo[1,5-a]pyrimidin-7-one,
2-methyl-5-methoxymethylpyrazolo[1,5-a]pyrimidin-7-one,
2-tert-butyl-5-trifluoromethylpyazolo[1,5-a]-pyrimidin-7-one,
and the addition salts thereof with an acid.

As examples of compounds of formula (Ib), mention may be made of those for which $R_1$, $R_2$, $R_3$ and $R_4$ have the same meanings as those mentioned in the examples of compounds of formula (Ia) defined above.

As compounds of formula (Ib) above, mention may be made most particularly of:
pyrazolo[1,5-a]pyrimidin-5-one,
2-methylpyrazolo[1,5-a]pyrimidin-5-one,
2,7-dimethylpyrazolo[1,5-a]pyrimidin-5-one,
2-phenylpyrazolo[1,5-a]pyrimidin-5-one,
2-ethylthiopyrazolo[1,5-a]pyrimidin-5-one,
2-carboxypyrazolo[1,5-a]pyrimidin-5-one,
7-aminopyrazolo[1,5-a]pyrimidin-5-one,
7-amino-2-methylpyrazolo[1,5-a]pyrimidin-5-one,
7-amino-2-phenylpyrazolo[1,5-a]pyrimidin-5-one,
7-amino-2-ethylthiopyrazolo[1,5-a]pyrimidin-5-one,
7-amino-2-carboxypyrazolo[1,5-a]pyrimidin-5-one,
and the addition salts thereof with an acid.

The compounds of the present invention and their processes are described in patent application EP-A-304,001.

Their synthetic intermediates are described in patent applications EP-A-591,103, WO 92/04349 and EP-A-320,764 and in the following publications:
C. Musants, Gazetta Chim. Ital 73, 355, 1943;
H. Dorn, Liebigs Ann. Chem. 707, 141, 1967;
H. Dorn, Liebigs Ann. Chem. 717, 118, 1968;
P. Arnold, Angew, Chem, Int. Ed., 13, 206, 1974;
K. Takahashi, Synthesis, 794, 1985;
C. B. Vicentini, Il Parmano, 47, (7, 8), 1021, 1992,
K. S. Hartke, J. Am. Chem. Soc., 81, 2456, 1959,
C. B. Vicentini, J. Het. Chem., 26, 797, 1989.

The compound(s) of formula (I) preferably represent(s) from 0.0005 to 12% by weight approximately relative to the total weight of the dye composition, and even more preferably from 0.005 to 6% by weight approximately relative to these weight.

The nature of the oxidation base(s) which can be used in the dye composition according to the invention is not critical. This or these oxidation bases is (are) preferably chosen from para-phenylenediamines, bis(phenyl) alkylenediamines, para-aminophenols, ortho-aminophenols and heterocyclic bases, and the addition salts thereof with an acid.

Among the para-phenylenediamines which can be used as oxidation bases in the dye composition according to the invention, mention may be made in particular of the compounds corresponding to formula (II) below:

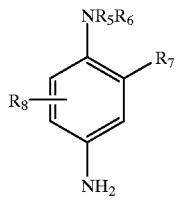

(II)

in which:

$R_5$ represents a hydrogen atom, a $C_1$–$C_4$ alkyl, $C_1$–$C_4$ monohydroxyalkyl, $C_2$–$C_4$ polyhydroxyalkyl or ($C_1$–$C_4$)alkoxy($C_1$–$C_4$)alkyl radical, $R_6$ represents a hydrogen atom or a $C_1$–$C_4$ alkyl, $C_1$–$C_4$ monohydroxyalkyl or $C_2$–$C_4$ polyhydroxyalkyl radical, $R_7$ represents a hydrogen atom, a halogen atom such as a chlorine atom, or a $C_1$–$C_4$ alkyl, sulpho, carboxyl, $C_1$–$C_4$ monohydroxylalkyl or $C_1$–$C_4$ hydroxyalkoxy radical, $R_8$ represents a hydrogen atom or a $C_1$–$C_4$ alkyl radical.

In formula (II) above, and when $R_7$ is other than a hydrogen atom, then $R_5$ and $R_6$ preferably represent a hydrogen atom and $R_7$ is preferably identical to $R_6$, and when $R_7$ represents a halogen atom, then $R_5$, $R_6$ and $R_8$ preferably represent a hydrogen atom.

Among the para-phenylenediamines of formula (II) above, mention may be made more particularly of para-phenylenediamine, para-toluylenediamine, 2-isopropyl-para-phenylenediamine, 2-β-hydroxyethoxy-para-phenylenediamine, 2,6-dimethyl-para-phenylenediamine, 2,6-diethyl-para-phenylenediamine, 4-amino-1-(β-methoxyethyl)aminobenzene and 2-chloro-para-phenylenediamine, and the addition salts thereof with an acid.

Among the bis(phenyl)alkylenediamines which can be used as oxidation bases in the dye composition according to the invention, mention may be made in particular of the compounds corresponding to formula (III) below, and the addition salts thereof with an acid:

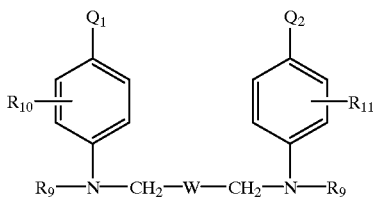
(III)

in which:

Q$_1$ and Q$_2$, which may be identical or different, represent a hydroxyl radical or a radical NHR$_{12}$ in which R$_{12}$ represents a hydrogen atom or a C$_1$–C$_4$ alkyl radical, R$_9$ represents a hydrogen atom or a C$_1$–C$_4$ alkyl, C$_1$–C$_4$ monohydroxylalkyl, C$_2$–C$_4$ polyhydroxyalkyl or C$_1$–C$_4$ aminoalkyl radical in which the amino residue may be substituted;

R$_{10}$ and R$_{11}$, which may be identical or different, represent a hydrogen or halogen atom or a C$_1$–C$_4$ alkyl radical, W represents a radical taken from the group consisting of the following radicals

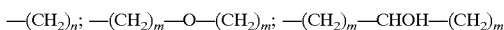

and

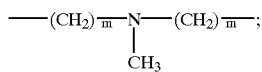

in which n is an integer between 0 and 8 inclusive and m is an integer between 0 and 4 inclusive.

Among the bis(phenyl)alkylenediamines of formula (III) above, mention may be made more particularly of N,N'-bis(β-hydroxyethyl)-N,N'-bis-(4'-aminophenyl)-1,3-diamino-2-propanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine and N,N'-bis(ethyl)-N,N'-bis(4'-amino-3'-methylphenyl)ethylenediamine, and the addition salts thereof with an acid.

Among these bis(phenyl)alkylenediamines of formula (III), N,N'-bis(β-hydroxyethyl)-N,N'-bis(4'-aminophenyl)-1,3-diaminopropanol or one of the addition salts thereof with an acid are particularly preferred.

Among the para-aminophenols which can be used as oxidation bases in the dye composition according to the invention, mention may be made in particular of the compounds corresponding to formula (IV) below, and the addition salts thereof with an acid:

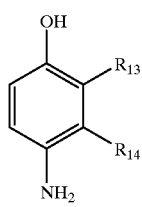
(IV)

in which:

R$_{11}$ represents a hydrogen atom or a C$_1$–C$_4$ alkyl, C$_1$–C$_4$ monohydroxyalkyl, (C$_1$–C$_4$)alkoxy(C$_1$–C$_4$)alkyl or C$_1$–C$_4$ aminoalkyl radical, R$_{14}$ represents a hydrogen or fluorine atom or a C$_1$–C$_4$ alkyl, C$_1$–C$_4$ monohydroxyalkyl, C$_2$–C$_4$ polyhydroxyalkyl, C$_1$–C$_4$ aminoalkyl, cyano(C$_1$–C$_4$) alkyl or (C$_1$–C$_4$)alkoxy(C$_1$–C$_4$)alkyl radical, it being understood that at least one of the radicals R$_{13}$ or R$_{14}$ represents a hydrogen atom.

Among the para-aminophenols of formula (IV) above, mention may be made more particularly to para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the addition salts thereof with an acid.

Among the ortho-aminophenols which can be used as oxidation bases in the dye composition according to the invention, mention may be made in particular to 2-aminophenol, 2-amino-1-hydroxy-5-methylbenzene, 2-amino-1-hydroxy-6-methylbenzene and 5-acetamido-2-aminophenol, and the addition salts thereof with an acid.

Among the heterocyclic bases which can be used as oxidation bases in the dye composition according to the invention, mention may be made in particular of pyridine derivatives, pyrimidine derivatives and pyrazole derivatives, and the addition salts thereof with an acid.

Among the pyridine derivatives, mention may be made more particularly of the compounds described, for example, in GB patents 1,026,978 and 1,153,196, such as 2,5-diaminopyridine, and the addition salts thereof with an acid.

Among the pyrimidine derivatives, mention may be made more particularly to compounds described, for example, in German patent DE 2,359,399 or Japanese patents JP 88-169, 5671 and JP 91-333,495, such as 2,3,5,6-tetraaminopyrimidine and 4-hydroxy-2,5,6-triaminopyrimidine and the addition salts thereof with an acid.

Among the pyrazole derivatives, mention may be made more particularly to the compounds described in patents DE 3,843,892 and DE 4,133,957 and patent applications WO 94/08969 and WO 94/08970, such as 4,5-diamino-1-methylpyrazole, 3,4-diaminopyrazole and 1-(4'-chlorobenzyl)-4,5-diaminopyrazole and the addition salts thereof with an acid.

According to the invention, the oxidation base(s) preferably represent(s) from 0.0005 to 12% by weight approximately relative to the total weight of the dye composition, and even more preferably from 0.005 to 6% by weight approximately relative to this weight.

The dye composition according to the invention can also contain one or more additional couplers other than the compounds of formula (I) and/or one or more direct dyes, so as to vary the shades obtained with the oxidation bases or to enrich the shades with glints.

The additional couplers which can be used in the composition according to the invention can be chosen from the couplers used conventionally in oxidation dyeing, and among which mention may be made in particular of meta-phenylenediamines, meta-aminophenols, meta-diphenols and heterocyclic couplers such as, for example, indole derivatives and indoline derivatives, and the addition salts thereof with an acid.

These couplers can be chosen in particular from 2-methyl-5-aminophenol, 5-N-(β-hydroxyethyl)amino-2-methylphenol, 3-aminophenol, 1,3-dihydroxybenzene, 1,3- dihydroxy-2-methylbenzene, 4-chloro-1,3-dihydroxybenzene, 2,4-diamino-1-(β-hydroxyethyloxy) benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole and 6-hydroxyindole, and the addition salts thereof with an acid.

When they are present, these additional couplers preferably represent from 0.0005 to 5% by weight approximately relative to the total weight of the dye composition, and even more preferably from 0.005 to 3% by weight approximately relative to this weight.

The addition salts with an acid for the oxidation bases(s) for the additional couplers which can be used in the dye composition of the invention are chosen in particular from the hydrochlorides, hydrobromides, sulphates, tartrates, lactases and acetates.

The medium which is suitable for dyeing (or the support) generally consists of water or of a mixture of water and at least one organic solvent for dissolving the compounds which would not be sufficiently water-soluble. As organic solvents, mention may be made, for example, of $C_1$–$C_4$ lower alcohols, such as ethanol and isopropanol; glycerol; glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

The solvents can be present in proportions preferably of between 1 and 40% by weight approximately relative to the total weight of the dye composition, and even more preferably between 5 and 30% by weight approximately.

The pH of the dye composition in accordance with the invention is generally between 3 and 12. It can be adjusted to the desired value using acidifying or basifying agents usually used to dye keratin fibres.

Among the acidifying agents, mention may be made, by way of example, of inorganic or organic acids such as hydrochloric acid, orthophosphoric acid, carboxylic acids such as tartaric acid, citric acid and lactic acid, and sulphonic acids.

Among the basifying agents, mention may be made, by way of example, of aqueous ammonia, alkaline carbonates, alkanolamines such as mono-, di- and triethanolamines and derivatives thereof, sodium hydroxide, potassium hydroxide and the compounds of formula (V) below:

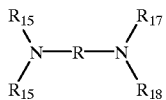
(V)

in which R is a propylene residue optionally substituted with a hydroxyl group or a $C_1$–$C_4$ alkyl radical; $R_{15}$, $R_{16}$, $R_{17}$ and $R_{18}$, which may be identical or different, represent a hydrogen atom or a $C_1$–$C_4$ alkyl or $C_1$–$C_4$ hydroxyalkyl radical.

The dye composition according to the invention can also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, conditioners such as, for example, silicones, film-forming agents, preserving agents and opacifiers.

Needless to say, the person skilled in the art will take care to select the optional complementary compound(s) mentioned above, such that the advantageous properties intrinsically associated with the dye composition according to the invention are not, or not substantially, adversely affected by the addition(s) envisaged.

The dye composition according to the invention can be in various forms, such as in the form of liquids, creams or gels or in any other form which is suitable for dyeing keratin fibres, and in particular human hair.

The subject of the invention is also the use of the pyrazolopyrimidinoxos of formula (I) above, as couplers, in combination with at least one oxidation base for the oxidation dyeing of keratin fibres, in particular human keratin fibres such as the hair.

Another subject of the invention is a process for the oxidation dyeing of keratin fibres, and in particular human keratin fibres such as the hair, using the dye composition as defined above.

According to this process, at least one dye composition as defined above is applied to the fibres, the colour being developed at acidic, neutral or alkaline pH using an oxidizing agent which is added to the dye composition only at the moment of use, or which is present in an oxidizing composition that is applied simultaneously or sequentially in a separate manner.

According to a particularly preferred embodiment of the dyeing process according to the invention, the dye composition described above is mixed, at the moment of use, with an oxidizing composition containing, in a medium which is suitable for dyeing, at least one oxidizing agent that is present in an amount which is sufficient to develop a coloration. The mixture obtained is then applied to the keratin fibres and is left to stand on them for 3 to 50 minutes approximately, preferably 5 to 30 minutes approximately, after which the fibres are rinsed, washed with shampoo, rinsed again and dried.

The oxidizing agent present in the oxidizing composition as defined above can be chosen from the oxidizing agents conventionally used for the oxidation dyeing of keratin fibres, and among which mention may be made of hydrogen peroxide, urea peroxide, alkali metal bromates and persalts such as perborates and persulphates. Hydrogen peroxide is particularly preferred.

The pH of the oxidizing composition containing the oxidizing agent as defined above is such that after mixing with the dye composition, the pH of the resulting composition applied to the keratin fibres preferably ranges between 3 and 12 approximately and even more preferably between 5 and 11. It is adjusted to the desired value using acidifying or basifying agents usually used to dye keratin fibres and as defined above.

The oxidizing composition as defined above can also contain various adjuvants conventionally used in compositions for dyeing the hair and as defined above.

The composition which is finally applied to the keratin fibres can be in various forms, such as in the form of liquids, creams or gels or in any other form which is suitable for dyeing keratin fibres, and in particular human hair.

Another subject of the invention is a dyeing "kit" or multi-compartment device or any other multi-compartment packaging system, in which a first compartment contains the dye composition as defined above and a second compartment contains the oxidizing composition as defined above.

These devices can be equipped with means which allow the desired mixture to be delivered onto the hair, such as the devices described in patent FR-2,586,913 in the name of the Applicant.

EXAMPLES

Examples 1 to 3 of Dyeing in Alkaline Medium

| Examples | 1 | 2 | 3 |
|---|---|---|---|
| 2,7-Dimethylpyrazolo[1,5-a]-pyrimidin-5-one (coupler) | 0.490 | 0.490 | — |
| 2,5-Dimethylpyrazolo[1,5-a]-pyrimidin-7-one (coupler) | — | — | 0.490 |
| Para-phenylenediamine (oxidation base) | 0.324 | 0.324 | 0.324 |
| Common dye support | No. 1 | No. 1 | No. 1 |
| Demineralized water qs | 100 g | 100 g | 100 g |

NB: The 2,7-dimethylpyrazolo[1,5-a]pyrimidin-5-one was prepared according to the process described in patent application EP-A-304,001, and the 2,5-dimethylpyrazolo[1,5-a] pyrimidin-7-one is sold under the trade name KM 00085 by the company Maybridge Common dye support No. 1:

| | |
|---|---|
| Benzyl alcohol | 2.0 g |
| Polyethylene glycol containing 6 mol of ethylene oxide | 3.0 g |
| Ethanol | 20.0 g |
| (C$_3$—C$_{10}$)Alkylpolyglucoside as an aqueous solution containing 60% active material, buffered with ammonium citrate, sold under the name Oramix CG110 by the company Seppic | 6.0 g |
| Aqueous ammonia containing 20% NH$_3$ | 10.0 g |
| Sodium metabisulphite | 0.228 g |
| Sequestering agent | qs |

At the moment of use, the dye composition of Example 1 above was mixed with an equal weight of 20-volumes hydrogen peroxide solution (6% by weight); each of the dye compositions of Examples 2 and 3 above was mixed with an equal weight of an aqueous ammonium persulphate solution at a concentration of 6×10$^{-3}$ mol %.

Each mixture obtained was applied for 30 minutes to locks of permanent-waved or non-permanent-waved natural grey hair containing 90% white hairs, at a rate of 10 g per 1 g of hair. After rinsing, washing with a standard shampoo and drying, the locks were dyed in the shades featured in Table 1 below:

TABLE 1

| Example | pH of the mixture | Shade obtained on natural grey hair containing 90% white hairs | Shade obtained on permanent-waved grey hair containing 90% white hairs |
|---|---|---|---|
| 1 | 9.9 | Iridescent | Slightly red iridescent |
| 2 | 10.1 | Iridescent | Iridescent bright red |
| 3 | 9.8 | Slightly golden very light blond | Slightly golden very light blond |

Example 4 of Dyeing in Neutral Medium

The following dye composition, in accordance with the invention, was prepared:

| | |
|---|---|
| 2,5-Dimethylpyrazolo[1,5-a]-pyrimidin-7-one | 0.490 g |
| Para-phenylenediamine | 0.324 g |
| Benzyl alcohol | 2.0 g |
| Polyethylene glycol 6 EO | 3.0 g |
| Ethanol | 20.0 g |
| (C$_3$—C$_{10}$)Alkylpolyglucoside as an aqueous solution containing 60% active material buffered with ammonium citrate, sold under the name Oramix CG110 by the company Seppic | 6.0 g |
| K$_2$HPO$_4$/KH$_2$PO$_4$ (1.5 M/1 M) buffer | 10.0 g |
| Sodium metabisulphite | 0.228 g |
| Sequestering agent | qs |

At the moment of use, the dye composition of Example 4 above was mixed with an equal weight of an aqueous ammonium persulphate solution at a concentration of 6×10$^{-3}$ mol %.

The mixture obtained had a pH of 7.2, and was applied for 30 minutes to locks of natural grey hair containing 90% white hairs, at a rate of 10 g per 1 g of hair. After rinsing, washing with a standard shampoo and drying, the locks were dyed in a slightly golden very light blond shade.

Examples 5 to 7 of Dyeing in Alkaline Medium

| Examples | 5 | 6 | 7 |
|---|---|---|---|
| 2-Methyl-5-methoxymethyl-pyrazolo[1,5-a]pyrimidin-7-one (coupler) | 0.579 | — | — |
| 2-tert-Butyl-5-trifluoromethylpyrazolo-[1,5-a]pyrimidin-7-one (coupler) | — | 0.777 | — |
| 2-Methyl-6-ethoxycarbonyl-pyrazolo[1,5-a]pyrimidin-7-one (coupler) | — | — | 0.663 |
| 1,3-Dimethyl-4,5-diamino-pyrazole dihydrochloride (oxidation base) | 0.597 | — | 0.597 |
| N,N-Bis(β-hydroxyethyl)-para-phenylenediamine dihydrochloride (oxidation base) | — | 0.807 | — |
| Common dye support | No. 1 | No. 1 | No. 1 |
| Demineralized water qs | 100 g | 100 g | 100 g |

NB: The 2-methyl-5-methoxymethylpyrazolo-[1,5-a] pyrimidin-7-one and 2-methyl-6-ethoxycarbonylpyrazolo[1, 5-a]pyrimidin-7-one are sold, respectively under the trade names KM 00739 and KM 00318 by the company Maybridge.

Common dye support No. 1:
This is identical to the one used for Examples 1 to 3 above.

At the moment of use, the dye compositions of Examples 5 to 6 above were mixed with an equal weight of 20-volumes hydrogen peroxide solution (6% by weight); the dye composition of Example 7 above was mixed with an equal weight of an aqueous ammonium persulphate solution at a concentration of 6×10$^{-3}$ mol %.

Each mixture obtained was applied for 30 minutes to locks of permanent-waved or non-permanent-waved natural grey hair containing 90% white hairs, at a rate of 10 g per 1 g of hair. After rinsing, washing with a standard shampoo and drying, the locks were dyed in the shades featured in Table 2 below:

TABLE 2

| Example | pH of the mixture | Shade obtained on natural grey hair containing 90% white hairs | Shade obtained on permanent-waved grey hair containing 90% white hairs |
|---|---|---|---|
| 5 | 9.9 | Very light rosewood | Light rosewood |
| 6 | 9.9 | Bottle green | Bottle green |
| 7 | 9.8 | Light golden blond | Light golden blond |

What is claimed is:

1. A composition for dyeing keratin fibers comprising, in a medium suitable for dyeing:
   (a) at least one coupler, wherein said coupler is at least one pyrazolopyrimidinoxo compound of formula (I) or an acid addition salt thereof:

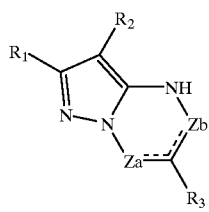

(I)

wherein:
   $R_1$ and $R_3$ are each independently chosen from a hydrogen atom; linear and branched $C_1$–$C_{20}$ alkyl radicals, unsubstituted or substituted with 1 or 2 radicals R; aryl radicals, unsubstituted or substituted with 1 or 2 radicals R; a 5- or 6-membered heterocycle having at least one heteroatom chosen from nitrogen, oxygen and sulphur atoms, unsubstituted or substituted with 1 or 2 radicals R;
   wherein R is chosen from halogen, nitro, cyano, hydroxyl, $C_1$–$C_4$ alkyl, haloalkyl, carboxyl, alkoxy, aryloxy, amino, alkylamino, acylamino, carbamoyl, sulphonamido, sulphamoyl, imido, alkylthio, arylthio, aryl, alkoxycarbonyl, and acyl;
   with the proviso that when $R_1$ is a linear or branched $C_1$–$C_{20}$ alkyl radical, an aryl radical or a 5- or 6-membered heterocycle, $R_1$ may be linked to the carbon atom of the ring via an oxygen, nitrogen or sulphur atom, such that $R_1$ is $XR_1$ wherein X is O, NH, or S;
   $R_1$ and $R_3$ can each independently also be chosen from a halogen atom; an acyl radical; a sulphonyl radical; a sulphinyl radical; a phosphonyl radical; a haloalkyl radical; a carbamoyl radical; a sulphamoyl radical; a cyano radical; a siloxy radical; an amino radical; an acylamino radical; an acyloxy radical; an alkoxy radical; an aryloxy radical; an alkylthio radical; a carbamoyloxy radical; a sulphonamide radical; an imide radical; a ureido radical; a sulphamoylamino radical; an alkoxycarbonylamino radical; an aryloxycarbonylamino radical; an alkoxycarbonyl radical; an aryloxycarbonyl radical; and a carboxyl radical;
   $R_2$ is chosen from a hydrogen atom; a halogen atom; an acetylamido group; an alkoxy radical; an aryloxy radical; an acyloxy radical; an arylthio radical; an alkylthio radical; a heteroarylthio radical; a heteroaryloxy radical; a thiocyano radical; an N,N-diethylthiocarbonylthio radical; a dodecyloxythiocarbonylthio radical; a benzenesulphonamido radical; an N-ethyltoluenesulphonamido radical; a pentafluorobutanamido radical; a 2,3,4,5,6-pentafluorobenzamido radical; a p-cyanophenylureido radical; an N,N-diethylsulphamoylamino radical; a pyrazolyl radical; an imidazolyl radical; a triazolyl radical; a tetrazolyl radical; a benzimidazolyl radical; a 1-benzyl-5-ethoxy-3-hydantoinyl radical; a 1-benzyl-3-hydantoinyl radical; 5,5-dimethyl-2,4-dioxo-3-oxazolidinyl; a 2-oxy-1, 2-dihydro-1-pyridyl radical; an alkylamido; an arylamido; a radical $NR^{III}R^{IV}$ wherein $R^{III}$ and $R^{IV}$ are independently chosen from a $C_1$–$C_4$ alkyl and a hydroxyalkyl; a carboxyl; and an alkoxycarboxylic radical; wherein all of said radicals may be substituted or unsubstituted, and
   $Z_a$ and $Z_b$ are different from each other and are chosen from a C=O group and $CR_4$ wherein $R_4$ independently has the same definition as given above for $R_1$; and (b) at least one oxidation base chosen from a para-phenylenediamine, a bis(phenyl)alkylenediamine, a para-aminophenol, an ortho-aminophenol, a heterocyclic base, and an acid addition salt thereof,
   wherein said para-phenylenediamine is a compound of formula (II) or an acid addition salt thereof:

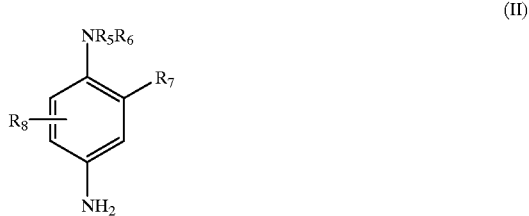

(II)

in which:
   $R_5$ is chosen from a hydrogen atom, a $C_1$–$C_4$ alkyl radical, a $C_1$–$C_4$ monohydroxyalkyl radical, a $C_2$–$C_4$ polyhydroxyalkyl radical, and a ($C_1$–$C_4$) alkoxy ($C_1$–$C_4$) alkyl radical;
   $R_6$ is chosen from a hydrogen atom, a $C_1$–$C_4$ alkyl radical, a $C_1$–$C_4$ monohydroxyalkyl radical, and a $C_2$–$C_4$ polyhydroxyalkyl radical;
   $R_7$ is chosen from a hydrogen atom, a halogen atom, a $C_1$–$C_4$ alkyl radical, a sulpho group, a carboxyl radical, a $C_1$–$C_4$ monohydroxyalkyl radical, and a $C_1$–$C_4$ hydroxalkoxy radical; and,
   $R_8$ is chosen from a hydrogen atom and a $C_1$–$C_4$ alkyl radical,
   with the proviso that said para-phenylenediamine of formula (II) is not 4-amino-3-methyl-N-ethyl-N-(β-hydroxyethyl)-aniline sulfate.

2. A composition according to claim 1, wherein said keratin fibers are human hair.

3. A composition according to claim 1, wherein $R_1$ is chosen from a hydrogen atom; linear and branched $C_1$–$C_4$ alkyl radicals; a phenyl; a phenyl substituted with a halogen atom, a $C_1$–$C_4$ alkyl, a $C_1$–$C_4$ alkoxy, a nitro group, an amino group, a trifluoromethyl group, or a $C_1$–$C_4$ alkylamino group; a benzyl radical; a benzyl radical substituted with a halogen atom, a $C_1$–$C_4$ alkyl, a $C_1$–$C_4$ alkoxy, a nitro group, an amino group, or a trifluoromethyl group; a $C_1$–$C_4$ alkylamino; thiophene; furan; pyridine; a trifluoromethyl radical; a radical $(CH_2)_p$—X—$(CH_2)_q$—OR' wherein p and q are independently chosen from integers ranging from 1 to 3, R' is chosen from H and methyl and X is chosen from an oxygen atom and a group NR" wherein R" is chosen from hydrogen and methyl; a $C_1$–$C_4$ hydroxyalkyl; a $C_1$–$C_4$ aminoalkyl; a $C_1$–$C_4$ alkylamino; a $C_1$–$C_4$ dialkylamino; an arylamino; methoxy; ethoxy; phenoxy; fluorine; chlorine; bromine; a carboxyl group; a ($C_1$–$C_4$)alkoxycarbonyl; a phenyloxycarbonyl; methylthio; ethylthio; phenylthio; methanesulphonyl; and cyano.

4. A composition according to claim 3, wherein $R_1$ is chosen from hydrogen; methyl; ethyl; isopropyl; tert-butyl; fluorine; chlorine; phenyl; toluyl; 4-chlorophenyl; 4-methoxyphenyl; 3-methoxyphenyl; 2-methoxyphenyl; benzyl; pyridyl; furyl; thienyl; trifluoromethyl; hydroxymethyl; aminomethyl; methoxy; ethoxy; methylamino; ethylamino; dimethylamino; carboxyl; methoxycarbonyl; ethoxycarbonyl; and cyano.

5. A composition according to claim 4, wherein $R_1$ is chosen from hydrogen; methyl; ethyl; phenyl; toluyl; 4-chlorophenyl; 4-methoxyphenyl; benzyl; trifluoromethyl; chloro; methoxy; ethoxy; carboxyl; methylamino; dimethylamino; and cyano.

6. A composition according to claim 1, wherein $R_2$ is chosen from a hydrogen atom; a $C_1$–$C_4$ alkoxy; phenoxy; phenoxy substituted with a halogen atom, a $C_1$–$C_4$ alkyl, a carboxyl, or a trifluoromethyl group; an acyloxy radical; benzyloxy; $C_1$–$C_4$ alkylthio; phenylthio; phenylthio substituted with a halogen atom, a $C_1$–$C_4$ alkyl, a carboxyl, or a trifluoromethyl group; a $C_1$–$C_4$ alkylamido; phenylamido; a radical $NR^{III}R^{IV}$ wherein $R^{III}$ and $R^{IV}$ are independently selected from a $C_1$–$C_4$ alkyl and a $C_1$–$C_4$ hydroxyalkyl; a carboxyl; and a $C_1$–$C_4$ alkoxycarboxylic radical.

7. A composition according to claim 1, wherein $R_2$ is chosen from hydrogen; chlorine; bromine; methoxy; ethoxy; phenyloxy; 4-methylphenyloxy; acyloxy; benzyloxy; methylthio, ethylthio; phenylthio; 4-methylphenylthio; 2-tert-butylphenylthio; acetamido; phenylacetamido; dimethylamino; diethylamino; ethylmethylamino; and (β-hydroxyethyl) methylamino.

8. A composition according to claim 7, wherein $R_2$ is chosen from hydrogen; chlorine; ethoxy; phenoxy; benzyloxy; acyloxy; acetamido; and dimethylamino.

9. A composition according to claim 1, wherein $R_3$ and $R_4$ are independently chosen from hydrogen; linear or branched $C_1$–$C_4$ alkyl, unsubstituted or substituted with a hydroxyl or an amino group; phenyl, unsubstituted or substituted with one or two groups chosen from halogen, $C_1$–$C_4$ alkyl, $C_1$–$C_4$ alkoxy, hydroxyl, carboxyl, nitro, $C_1$–$C_4$ alkylthio, methylenedioxy, amino, trifluoromethyl, and $C_1$–$C_4$ alkylamino; benzyl, unsubstituted or substituted with a halogen, a methyl, an isopropyl or methoxy; $C_1$–$C_4$ hydroxyalkyl; $C_1$–$C_4$ aminoalkyl; $C_1$–$C_4$ alkylaminoalkyl; amino; $C_1$–$C_4$ alkylamino; halogen; and trifluoromethyl.

10. A composition according to claim 1, wherein $R_3$ and $R_4$ are independently chosen from hydrogen; $C_1$–$C_4$ alkyl; halogen; amino; $C_1$–$C_4$ alkylamino; aryl; benzyl; hydroxymethyl; hydroxyethyl; aminomethyl; aminoethyl; and trifluoromethyl.

11. A composition according to claim 1, wherein $R_3$ and $R_4$ are independently chosen from hydrogen, methyl, ethyl, isopropyl, trifluoromethyl, chlorine, amino, methylamino, ethylamino, phenyl, 4-chlorophenyl, and 4-methoxyphenyl.

12. A composition according to claim 1, wherein said at least one pyrazolopyrimidinoxo compound is chosen from:
    (i) a pyrazolo[1,5-a]pyrimidin-7-oxo compound of formula (Ia):

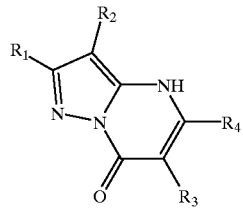

(Ia)

and (ii) a pyrazolo[1,5-a]pyrimidin-5-oxo compound of formula (Ib):

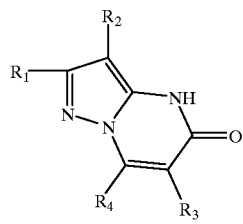

wherein $R_1$, $R_2$, $R_3$, and $R_4$ are as defined in claim 1.

13. A composition according to claim 12, wherein said at least one pyrazolopyrimidinoxo compound is a pyrazolo[1,5-a]pyrimidin-7-oxo compound of formula (Ia) wherein:
    $R_1$ is chosen from hydrogen, methyl, ethyl, chlorine, phenyl, methoxy, trifluoromethyl, carboxyl, and cyano;
    $R_2$ is chosen from hydrogen, chlorine, and ethoxy;
    $R_3$ and $R_4$ respectively are chosen from hydrogen and hydrogen; hydrogen and methyl; methyl and hydrogen; hydrogen and amino; chlorine and methyl; chlorine and amino; carboxyl and methyl; hydrogen and trifluoromethyl; and carboxyl and hydrogen.

14. A composition according to claim 12, wherein said at least one pyrazolopyrimidinoxo compound is a pyrazolo[1,5-a]pyrimidin-5-oxo compound of formula (Ib), wherein:
    $R_1$ is chosen from hydrogen, methyl, ethyl, chlorine, phenyl, methoxy, trifluoromethyl, carboxyl, and cyano;
    $R_2$ is chosen from hydrogen, chlorine, and ethoxy;
    $R_3$ and $R_4$ respectively are chosen from hydrogen and hydrogen; hydrogen and methyl; methyl and hydrogen; hydrogen and amino; chlorine and methyl; chlorine and amino; carboxyl and methyl; hydrogen and trifluoromethyl; and carboxyl and hydrogen.

15. A composition according to claim 1, wherein said at least one pyrazolopyrimidinoxo compound is chosen from:
    pyrazolo[1,5-a]pyrimidin7-one,
    2-methylpyrazolo[1,5-a]pyrimidin-7-one,
    2-phenylpyrazolo[1,5-a]pyrimidin-7-one,
    2-carboxypyrazolo[1,5-a]pyrimidin-7-one,
    2-ethylthiopyrazolo[1,5-a]pyrimidin-7-one,
    2,5-dimethylpyrazolo[1,5-a]pyrimidin-7-one,
    2-phenyl-5-methylpyrazolo[1,5-a]pyrimidin-7-one,
    2-carboxy-5-methylpyrazolo[1,5-a]pyrimidin-7-one,
    2-ethylthio-5-methylpyrazolo[1,5-a]pyrimidin-7-one,
    2-methyl-5-trifluoromethylpyrazolo[1,5-]pyrimidin-7-one,
    2-phenyl-5-trifluoromethylpyrazolo[1,5-a]pyrimidin-7-one, 2-carboxy-5-trifluoromethylpyrazolo[1,5-a]pyrimidin-7-one,
2-ethylthio-5-trifluoromethylpyrazolo[1,5-a]pyrimidin-7-one,
5-trifluoromethylpyrazolo[1,5-a]pyrimidin-7-one,
5-methylpyrazolo[1,5-a]pyrimidin-7-one,
6-carboxypyrazolo[1,5-a]pyrimidin-7-one,
6-carboxy-2-methylpyrazolo[1,5-a]pyrimidin-7-one,
6-carboxy-2-phenylpyrazolo[1,5-a]pyrimidin-7-one,
6-carboxy-2-ethylthiopyrazolo[1,5-a]pyrimidin-7-one,
2,6-dicarboxypyrazolo[1,5-a]pyrimidin-7-one,
2-methyl-6-ethoxycarbonylpyrazolo[1,5-a]pyrimidin-7-one,
2-(2'-furyl)-6-methylpyrazolo[1,5-]pyrimidin-7-one,
2-(2'-thienyl)-6-methylpyrazolo[1,5-a]pyrimidin-7-one,
3-ethoxycarbonyl-6-methylpyrazolo[1,5-a]pyrimidin-7-one,
2-methyl-5-methoxymethylpyrazolo[1,5-a]pyrimidin-7-one,
2-tert-butyl-5-trifluoromethylpyrazolo[1,5-a]pyrimidin-7-one,
pyrazolo[1,5-a]pyrimidin-5-one,
2-methylpyrazolo[1,5-a]pyrimidin-5-one,
2,7-dimethylpyrazolo[1,5-a]pyrimidin-5-one,
2-phenylpyrazolo[1,5-a]pyrimidin-5-one,
2-ethylthiopyrazolo[1,5-a]pyrimidin-5-one,
2-carboxypyrazolo[1,5-a]pyrimidin-5-one,
7-aminopyrazolo[1,5-a]pyrimidin-5-one,
7-amino-2-methylpyrazolo[1,5-a]pyrimidin-5-one,
7-amino-2-phenylpyrazolo[1,5-a]pyrimidin-5-one,
7-amino-2-ethylthiopyrazolo[1,5-a]pyrimidin-5-one, or
7-amino-2-carboxypyrazolo[1,5-a]pyrimidin-5-one,
and an acid addition salt thereof.

16. A composition according to claim 1, wherein said at least one coupler is chosen from hydrochloride, hydrobromide, tartrate, tosylate, benzenesulphonate, sulphate, lactate, and acetate acid addition salts.

17. A composition according to claim 1, wherein said at least one pyrazolopyrimidinoxo compound is present in an amount ranging from about 0.0005 to about 12% by weight relative to the total weight of said composition.

18. A composition according to claim 17, wherein said at least one pyrazolopyrimidinoxo compound is present in an amount ranging from about 0.005 to about 6% by weight relative to the total weight of said composition.

19. A composition according to claim 1, wherein said at least one oxidation base is present in an amount ranging from about 0.0005 to about 12% by weight relative to the total weight of said composition.

20. A composition according to claim 19, wherein said at least one oxidation base is present in an amount ranging from about 0.005 to about 6% by weight relative to the total weight of said composition.

21. A composition according to claim 1, wherein said composition further comprises at least one additional coupler or an acid addition salt thereof, other than said at least one pyrzolopyrimidinoxo compound of formula (I); at least one direct dye; or both.

22. A composition according to claim 1, wherein said at least one oxidation base is chosen from hydrochloride, hydrobromide, sulphate, tartrate, lactate, and acetate acid addition salts.

23. A composition according to claim 21, wherein said at least one additional coupler is chosen from hydrochloride, hydrobromide, sulphate, tartrate, lactate, and acetate acid addition salts.

24. A composition according to claim 1, wherein said medium suitable for dyeing comprises water or a mixture of water and at least one organic solvent.

25. A composition according to claim 24, wherein the medium comprises a mixture of water and at least one organic solvent which is chosen from a $C_1$–$C_4$ lower alcohol, glycerol, glycol, glycol ether, and an aromatic alcohol.

26. A composition according to claim 24, wherein said at least one organic solvent is present in an amount ranging from about 1 to about 40% by weight relative to the total weight of said composition.

27. A composition according to claim 26, wherein said at least one organic solvent is present in an amount ranging from about 5 to about 30% by weight relative to the total weight of said composition.

28. A composition according to claim 1, wherein said composition has a pH ranging from about 3 to about 12.

29. A composition according to claim 1, wherein said composition further comprises at least one cosmetically acceptable additive.

30. A composition according to claim 1, wherein said composition is in the form of a liquid, a cream, or a gel.

31. A multi-compartment dyeing kit, comprising a first compartment containing at least one composition for dyeing keratin fibers and a second compartment containing at least one oxidizing composition, wherein said at least one composition for dyeing keratin fibers comprises, in a medium suitable for dyeing:
(a) at least one coupler, wherein said coupler is at least one pyrazolopyrimidinoxo compound of formula (I) or an acid addition salt thereof:

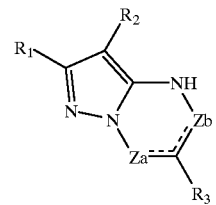

(I)

$R_1$ and $R_3$ are each independently chosen from a hydrogen atom; linear and branched $C_1$–$C_{20}$ alkyl radicals, unsubstituted or substituted with 1 or 2 radicals R; aryl radicals, unsubstituted or substituted with 1 or 2 radicals R; a 5- or 6-membered heterocycle having at least one heteroatom chosen from nitrogen, oxygen and sulphur atoms, unsubstituted or substituted with 1 or 2 radicals R;

wherein R is chosen from halogen, nitro, cyano, hydroxyl, $C_1$–$C_4$ alkyl, haloalkyl, carboxyl, alkoxy, aryloxy, amino, alkylamino, acylamino, carbamoyl, sulphonamido, sulphamoyl, imido, alkylthio, arylthio, aryl, alkoxycarbonyl, and acyl;

with the proviso that when $R_1$ is a linear or branched $C_1$–$C_{20}$ alkyl radical, an aryl radical or a 5- or 6-membered heterocycle, $R_1$ may be linked to the carbon atom of the ring via an oxygen, nitrogen or sulphur atom, such that $R_1$ is $XR_1$ wherein X is O, NH, or S;

R₁ and R₃ can each independently also be chosen from a halogen atom; an acyl radical; a sulphonyl radical; a sulphinyl radical; a phosphonyl radical; a haloalkyl radical; a carbamoyl radical; a sulphamoyl radical; a cyano radical; a siloxy radical; an amino radical; an acylamino radical; an acyloxy radical; an alkoxy radical; an aryloxy radical; an alkylthio radical; a carbamoyloxy radical; a sulphonamide radical; an imide radical; a ureido radical; a sulphamoylamino radical; an alkoxycarbonylamino radical; an aryloxycarbonylamino radical; an alkoxycarbonyl radical; an aryloxycarbonyl radical; and a carboxyl radical;

R₂ is chosen from a hydrogen atom; a halogen atom; an acetylamido group; an alkoxy radical; an aryloxy radical; an acyloxy radical; an arylthio radical; an alkylthio radical; a heteroarylthio radical; a heteroaryloxy radical; a thiocyano radical; an N,N-diethylthiocarbonylthio radical; a dodecyloxythiocarbonylthio radical; a benzenesulphonamido radical; an N-ethyltoluenesulphonamido radical; a pentafluorobutanamido radical; a 2,3,4,5,6-pentafluorobenzamido radical; a p-cyanophenylureido radical; an N,N-diethylsulphamoylamino radical; a pyrazolyl radical; an imidazolyl radical; a triazolyl radical; a tetrazolyl radical; a benzimidazolyl radical; a 1-benzyl-5-ethoxy-3-hydantoinyl radical; a 1-benzyl-3-hydantoinyl radical; 5,5-dimethyl-2,4-dioxo-3-oxazolidinyl; a 2-oxy-1,2-dihydro-1-pyridyl radical; an alkylamido; an arylamido; a radical $NR^{III}R^{IV}$ wherein $R^{III}$ and $R^{IV}$ are independently chosen from a $C_1$–$C_4$ alkyl and a hydroxyalkyl; a carboxyl; and an alkoxycarboxylic radical; wherein all of said radicals may be substituted or unsubstituted, and $Z_a$ and $Z_b$ are different from each other and are chosen from a C=O group and $CR_4$ wherein $R_4$ independently has the same definition as given above for $R_1$; and (b) at least one oxidation base chosen from a para-phenylenediamine, a bis(phenyl)alkylenediamine, a para-aminophenol, an ortho-aminophenol, a heterocyclic base, and an acid addition salt thereof, wherein said para-phenylenediamine is a compound of formula (II) or an acid addition salt thereof:

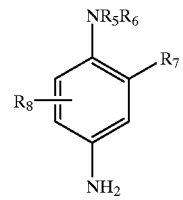

(II)

in which:

$R_5$ is chosen from a hydrogen atom, a $C_1$–$C_4$ alkyl radical, a $C_1$–$C_4$ monohydroxyalkyl radical, a $C_2$–$C_4$ polyhydroxyalkyl radical, and a ($C_1$–$C_4$) alkoxy ($C_1$–$C_4$) alkyl radical;

$R_6$ is chosen from a hydrogen atom, a $C_1$–$C_4$ alkyl radical, a $C_1$–$C_4$ monohydroxylalkyl radical, and a $C_2$–$C_4$ polyhydroxyalkyl radical;

$R_7$ is chosen from a hydrogen atom, a halogen atom, a $C_1$–$C_4$ alkyl radical, a sulpho group, a carboxyl radical, a $C_1$–$C_4$ monohydroxylalkyl radical, and a $C_1$–$C_4$ hydroxalkoxy radical; and, $R_8$ is chosen from a hydrogen atom and a $C_1$–$C_4$ alkyl radical, with the proviso that said para-phenylenediamine of formula (II) is not 4-amino-3-methyl-N-ethyl-N-(β-hydroxyethyl)-aniline sulfate.

* * * * *

UNITED STATES PATENT AND TRADEMARK OFFICE
CERTIFICATE OF CORRECTION

PATENT NO.    : 6,379,395 B1
DATED         : April 30, 2002
INVENTOR(S)   : Laurent Vidal et al.

It is certified that error appears in the above-identified patent and that said Letters Patent is hereby corrected as shown below:

Title page,
Item [57], ABSTRACT,
Line 6, after "with" insert -- : --.
Line 8, after "halogen," insert -- . . . --.

Column 15,
Line 40, before "methylamino" delete the space.

Column 16,
Line 64, "[1,5-]" should read -- [1,5-a] --.

Column 17,
Line 16, "[1,5-]" should read -- [1,5-a] --.

Column 18,
After formula (I), line 48, insert -- wherein: --.

Signed and Sealed this

Twenty-second Day of October, 2002

Attest:

JAMES E. ROGAN
Attesting Officer    Director of the United States Patent and Trademark Office